(12) United States Patent
Kobayashi et al.

(10) Patent No.: US 7,191,014 B2
(45) Date of Patent: Mar. 13, 2007

(54) LIVING BODY STIMULATING APPARATUS

(75) Inventors: Tatsuyuki Kobayashi, Niigata-ken (JP); Takashi Izumi, Niigata-ken (JP)

(73) Assignee: Techno Link Co., Ltd. (JP)

( * ) Notice: Subject to any disclaimer, the term of this patent is extended or adjusted under 35 U.S.C. 154(b) by 603 days.

(21) Appl. No.: 10/624,867

(22) Filed: Jul. 22, 2003

(65) Prior Publication Data

US 2004/0236391 A1 Nov. 25, 2004

(30) Foreign Application Priority Data

May 23, 2003 (JP) .............................. 2003-145653

(51) Int. Cl.
*A61N 1/00* (2006.01)
(52) U.S. Cl. ..................................................... 607/72
(58) Field of Classification Search ............. 607/68–74
See application file for complete search history.

(56) References Cited

U.S. PATENT DOCUMENTS

| | | | |
|---|---|---|---|
| 5,222,492 A * | 6/1993 | Morgan et al. ................. | 607/5 |
| 5,871,506 A * | 2/1999 | Mower ........................... | 607/9 |
| 6,298,266 B1 * | 10/2001 | Rubin et al. ................... | 607/5 |
| 6,526,319 B2 | 2/2003 | Kobayashi | |
| 6,535,767 B1 * | 3/2003 | Kronberg ...................... | 607/72 |
| 2002/0010495 A1 | 1/2002 | Freed et al. | |

* cited by examiner

*Primary Examiner*—Mark Bockelman
(74) *Attorney, Agent, or Firm*—Akerman Senterfitt

(57) ABSTRACT

A living body stimulating apparatus capable of giving extensive therapeutic effects and softer feeling of stimulation. Rectangular wave pulse groups S containing a plurality of pulse density modulated higher frequency components or on-pulses than a rectangular wave pulse are applied repeatedly from conductor elements 24 to a human body. As a human body has a capacitive impedance, softer stimulation can be applied to the human body as compared with a rectangular wave having the same current and frequency. Furthermore, a pause period between on-pulses is varied by a stimulus generator means 8, so that a charging current to an equivalent electrostatic capacity of a human body is supplied little by little so as to slowly increase a charged quantity. As a result, cenesthesia of softer stimulation can be obtained.

11 Claims, 5 Drawing Sheets

FIG. 3  Waveform in the case where the apparatus is connected to a 500 Ω resistor.
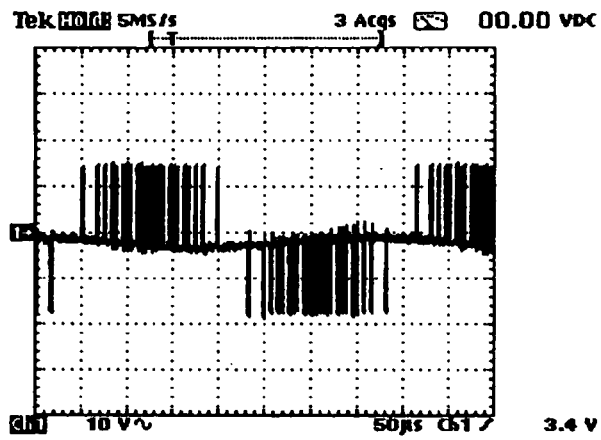
FIG. 4  Waveform showing enlarged half cycle waveforms in FIG.3.
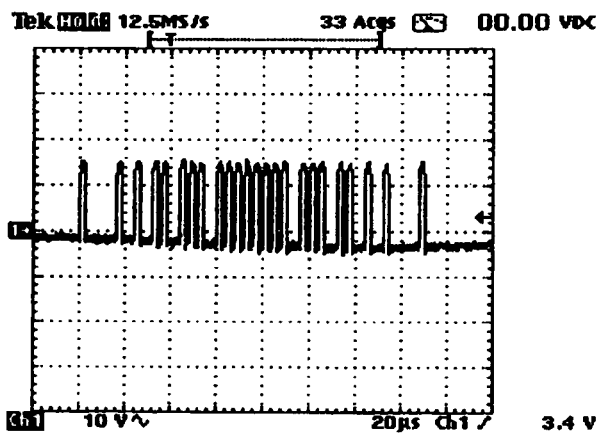
FIG. 5  Waveform in the case where the apparatus is attached to a human waist.
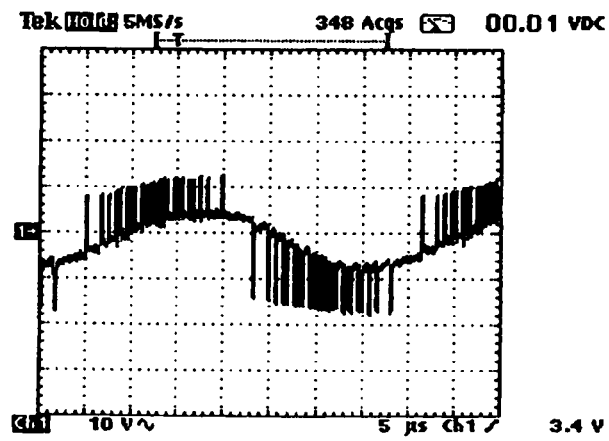

LIVING BODY STIMULATING APPARATUS

BACKGROUND OF THE INVENTION

1. Field of the Invention

The present invention relates to a living body stimulating apparatus. More particularly, the present invention concerns a stimulating apparatus of the kind comprising a conductor element with a built-in electrode which can be attached to a living body. Stimulation is achieved by an electric current flowing through the electrode into the living body.

2. Description of the Related Art

A conventional living body stimulating apparatus is used for the treatment of a nerve function in a diseased part, by allowing a low frequency pulse current to flow in the diseased part, such low frequency pulse current being output from a transmitter to an electrode. In Japanese Patent Un-examined Publication No. 1-146562, for example, is disclosed a living body stimulating apparatus which enables the control of the speed and intensity of stimulation, by switching stimulation signals output from an output circuit to a living body (or human body). The stimulation signals are either DC intermittent pulses for periodically outputting positive pulses, AC intermittent pulses for periodically outputting rectangular wave pulse groups consisting of positive pulses and negative pulses, alternate intermittent pulses for periodically and alternately outputting positive pulses and negative pulses, the period or amplitude of which can be varied.

However, it is generally difficult to make pass a DC current through a human body, since it has a resistance of about 100 KΩ, depending upon voltage, whilst a high-frequency AC current flows easily through a human body. For example, a human body exhibits a resistance of about 1 KΩ under an AC voltage of 1 KHz, the resistance being reduced by half if the frequency doubles. In other word, a human body has a capacitive impedance and thus the in-vivo resistance tends to decrease as frequency increases. On the other hand, as the stimulation of the human body is concerned, low frequencies close to direct current, and rectangular waves comprising a high DC component are more stimulative. Thus, for the same frequency, sinusoidal waves will induce softer stimuli than rectangular waves.

FIG. 7 illustrates an example of a conventional living body stimulating apparatus for applying stimulation signals having the form of sine waves to a human body. As shown, numeral 101 designates a CPU (central processing unit) as controlling means. The CPU outputs digital data signals which are converted into analogue data signals by a D/A converter circuit 102. Then, the analogue data signals are amplified by an amplifier 103, to provide sine-wave stimulation signals across conductive elements or output electrodes 105, via a transformer 104. The amplitude of the sine wave can be increased or decreased arbitrarily by operating a variable gain element 106 at the input of the amplifier 103.

Although a sinusoidal wave induces a soft stimulation of the human body and is agreeable thereto, it comprises only one frequency component, which leads to a very limited therapeutic effect. Furthermore, the output circuit of such a conventional apparatus requires analogue circuits such as the D/A converter 102 and the amplifier 103 which are necessary for obtaining a substantially sinusoidal waveform. The number of components is relatively high and the circuitry is complex, thus leading to low power efficiency and high manufacturing costs. In other words, conventional circuits outputting sinusoidal waves would require dozens of components such as transistors, resistors and capacitors.

In an effort to solve these problems, Japanese Patent Un-examined Publication No. 2001-259048 previously filed by the present applicant proposed a living body stimulation apparatus. The conventional apparatus is provided with a stimulus generator means for applying pulse-width modulation to rectangular wave pulses that are output at predetermined recurrence frequency, and then recurringly outputting rectangular wave pulse groups containing a plurality of higher frequency components than the rectangular wave pulse to the electrodes as stimulation signals. In the conventional apparatus, PWM is adopted so that a time width of each on-pulse gradually increases during the first half of the rectangular wave pulse group and then gradually decreases during the second half thereof as it comes closer to the falling edge of the rectangular wave pulse group. As a result, the waveform of the rectangular wave pulse group applied to a human body is distorted to form an approximately sinusoidal wave, which can give soft feeling of stimulation to a human body.

In the above second Patent Publication, the time width of each on-pulse constituting the rectangular wave pulse group is gradually increased and then gradually decreased by means of PWM, and then, thus modulated rectangular wave pulse group which has alternately a positive voltage or a negative voltage, is applied to a human body to be distorted by a capacitive element of the human body, so that stimulation signals are deformed into waveforms approximate to sinusoidal waves of low frequency, thus giving soft feeling of stimulation. Since the time width of each on-pulse, however, is varied for example in a range of from 10 μsec to 60 μsec during the generation of the rectangular pulse groups, the time width of the on-pulse is likely to becomes too large partially, so that a charged quantity in equivalent electrostatic capacity of a human body rises rapidly, resulting in a drawback that cenesthesia of soft stimulation is hard to obtain.

SUMMARY OF THE INVENTION

It is a main object of the present invention to solve the problems recited above and to propose a living body stimulating apparatus that can provide extensive therapeutic effects and softer feeling of stimulation.

To attain the above objects, there is proposed a living body stimulating apparatus as defined in the appended claims.

According to a first aspect of the present invention, there is provided a living body stimulating apparatus for applying an electric stimulus to a living body, said apparatus comprising conductor elements to apply a stimulation signal to said living body by allowing an electric current to flow from the conductor elements to said living body, wherein said apparatus further comprises:

a stimulus generator means for recurringly outputting rectangular wave pulse groups to said conductor elements as stimulation signals, said stimulus generator means outputting the stimulation signals in which the density of a plurality of on-pulses that constitute the rectangular wave pulse groups is varied during an output period of the rectangular wave pulse groups.

According to the above structure, when the rectangular wave pulse groups containing a plurality of on-pulses are repeatedly output to the conductor elements as stimulation signals, the human body functions as if it were a capacitive element and thus the impedance of the human body is lowered by the on-pulses that are high frequency signal components, so that the rectangular wave pulse groups are distorted to take the waveforms of low frequencies as a whole inside the human body. Accordingly, softer feeling of stimulation is obtained as compared with the rectangular waveforms of the same current and frequency. In addition, since each of the rectangular pulse groups includes higher frequency signal components than the rectangular wave pulse, extensive therapeutic effects can be obtained by the signal components.

Moreover, since the stimulus generator means arbitrarily varies the density of a plurality of the on-pulses that constitute the rectangular pulse groups, a low frequency waveform inside a living body can be distorted so as to be in a desirable state according to the on-pulse density level. Besides, as the time width of each on-pulse is constant, while a pause period between the on-pulses is varied by the stimulus generator means during the output period of each rectangular pulse group, there will exist no on-pulses wider than other on-pulses, which in turn means that a charging current is supplied little by little relative to the equivalent electrostatic capacity of a living body to thereby raise a charged quantity slowly, so that the cenesthesia of softer stimulation can be obtained.

According to a second aspect of the present invention, there is provided a living body stimulating apparatus according to the first aspect, wherein the stimulus generator means alternately outputs the positive rectangular wave pulse groups and the negative rectangular wave pulses groups each of which having a preset time width as a whole, said preset time width being defined from a rising edge of each pulse group to a falling edge thereof, and wherein the density of the on-pulses gradually increases from the rising edge until the first half of the preset time width elapses, and then gradually decreases as they come closer to the falling edge during the second half thereof.

Accordingly, the waveform of each rectangular pulse group is distorted so that the resultant stimulation signals take the waveforms where high frequency on-pulses are superimposed upon the signals that are approximate to low frequency sinusoidal waves. Thus, not only can the extensive therapeutic effects be obtained but also can the cenesthesia of softer stimulation be produced as compared to the rectangular wave of the same current and frequency, due to the absence of wider on-pulses and the slow increase in a charged quantity in an equivalent electrostatic capacity of the living body.

According to a third aspect of the present invention, there is provided a living body stimulating apparatus according to one of the foregoing aspects, wherein the stimulus generator means outputs the stimulation signals so that the time width of the rectangular wave pulse group may be at least 100 times as wide as that of each on-pulses.

Accordingly, to a living body is applied each on-pulse having the time width shorter than one hundredth of that of the rectangular wave pulse group composed of an group of the on-pulses, and thus high frequency signal components can be extremely effectively applied to a living body during the generation of low frequency signal components.

BRIEF DESCRIPTION OF THE DRAWING

For more complete understanding of the present invention, reference is now made to the following description taken in conjunction with the accompanying drawings, in which:

FIG. 3 is a waveform diagram of a stimulating signal when a dummy resistance is connected across the conductor elements of the apparatus.

FIG. 4 shows enlarged half cycle waveforms in FIG. 3.

FIG. 5 shows a waveform diagram of a stimulating signal when the conductive elements are attached to a human waist.

DESCRIPTION OF THE PREFFERED INVENTION

Figure 1:
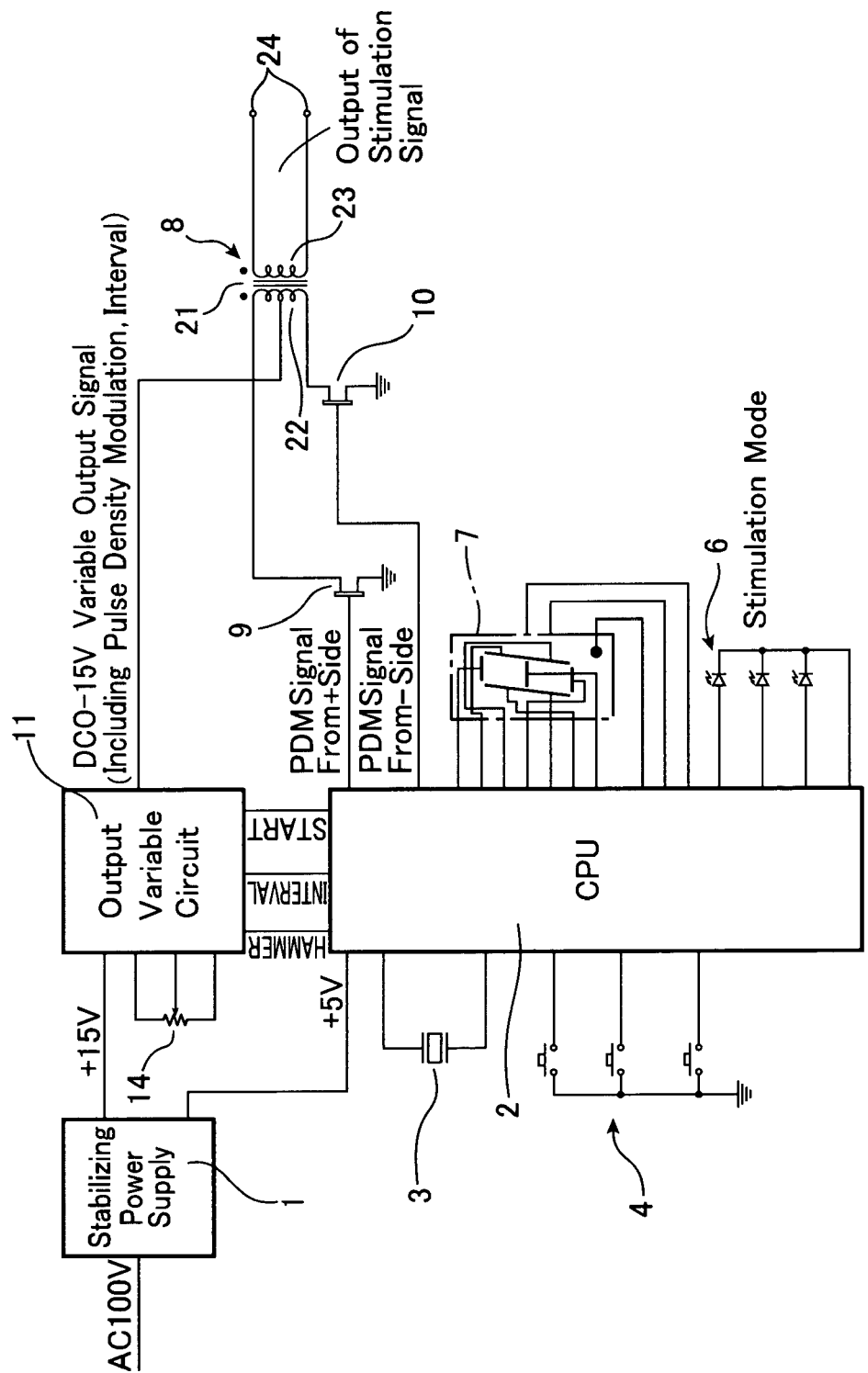
FIG. 1 is a circuit diagram showing a living body stimulating apparatus in accordance with an embodiment of the present invention.

Hereunder is a description of an embodiment of a living body stimulating apparatus proposed by the present invention with reference to the appended drawings.

First, an overall configuration of an apparatus of the present invention will be described with reference to FIG. 1. Reference numeral 1 designates a stabilized power supply unit for converting AC input into a stabilized DC output. In the embodiment, AC source voltage of 100V is converted into DC voltages of +15V and DC +5V, respectively. Reference numeral 2 designates a CPU (central processing unit) serving as a control means powered by the DC +5V from the stabilized power supply unit 1. The CPU operates by reference clock signals from a crystal oscillator 3. As well known in the art, CPU 2 is integrated with an input/output means, a processing means and a memory means in which a control sequence is stored, said control sequence being able to generate predetermined patterns of stimulating electric current flowing into a human body (not shown) as a living body.

To input ports of the CPU 2 are connected a plurality of switches 4 for selecting a specific stimulation mode from among several stimulation modes. On the other hand, to output ports thereof are connected a plurality of LEDs 6 for displaying which stimulation mode is currently active. Furthermore, to the output ports of the CPU 2 are connected a segment LED 7 as a time display means for counting and displaying the stimulation time, two FETs 9, 10 constituting the stimulus generator means 8 and an output-variable circuit 11 for varying the amplitude and time interval (pause period) of the stimulating signals to be applied to a human body. For the sake of simplicity, only one segment LED 7 is illustrated in the present embodiment. However, two or more segment LEDs 7 could be connected in parallel. Alternatively, the foregoing LEDs 6 and the segment LED 7 may be integrated together in a common LCD display.

The output-variable circuit 11 is powered by the DC voltage of DC +15V provided by the stabilized power source 1 and receives control signals from the CPU 2, namely the strong stimulation command signal (HAMMER), the stimulation pause setting signal (INTERVAL), the stimulation start signal (START) and the output level setting signal from a manually operable variable resister 14. As a result, the output-variable circuit 11 supplies, to the stimulus generator means 8, rectangular-wave-formed variable output signals that are generated in a predetermined recurrent frequency and are subjected to amplitude modulation between DC 0V and DC +15V.

The stimulus generator means 8 subjects the variable output signal from the output-variable circuit to pulse density modulation. The stimulus generator comprises FETs 9, 10 serving as switching means and a transformer 21 with primary and secondary windings thereof insulated from each other. More specifically, the primary winding 22 of the transformer 21 has a center tap connected to a variable output signal line of the output-variable circuit 11, while a pair of output electrodes 24 serving as conductive elements are connected across the secondary winding 23 for outputting the stimulation signals. One end of the primary winding 22 of the transformer 21 is connected to a drain of the source-grounded FET 9, while the other end of the primary winding 22 of the transformer 21 is connected to a drain of the source-grounded FET 10. The +side PDM (Pulse Density Modulation) signals from the CPU 2 are supplied to a gate that is a control terminal of the FET 9, while the-side PDM signals from the CPU 2 are supplied to a gate that is a control terminal of the FET 10.

Next, the behavior of the above-configured apparatus will be described with reference to the waveform diagram shown in FIG. 2, in which the uppermost waveform shows a variable output signal from the output-variable circuit 11, followed by the respective waveforms of the +side PDM signals, −side PDM signals and the stimulation signals across the output electrodes 24.

If a specific stimulation mode is selected by the switch 4, and then a start switch (not shown) is operated, the LED 6 corresponding to the specific stimulation mode selected is switched on by the CPU 2. The CPU 2 controls the stimulus generator means 8 and the output-variable circuit 11 in order that the stimulation signals corresponding to the selected stimulation mode are output across the electrodes 24. The stimulation start signal is supplied from the CPU 2 to the output-variable circuit 11 and the variable output signal is supplied from the output-variable circuit 11 to the stimulus generator means 8. As shown on the left side in FIG. 2, the variable output signal comprises rectangular wave pulses defined by an amplitude A1 and a time width t1, repeating at a period T. The amplitude A1 can be varied by operating the variable resistor 14 in the range DC 0V to DC +15V, thus making it easy for a user to change the degree of stimulation to a desired level. Alternatively, the period T and time width t1 can be varied by the CPU 2 (not shown in the drawings). In such an embodiment a user may obtain a more desirable stimulus by varying a parameter of the control program installed inside the CPU 2.

Every time a rectangular wave pulse is output from the output-variable circuit 11, the CPU 2 is enabled to output a plurality of on-pulses alternately to the FET 9 or to the FET 10 during the output period of the rectangular wave pulse. The on-pulses contain a higher frequency component than the rectangular wave pulse. The time interval t2 (off-time interval) between the on-pulse outputs to the FET 9 or FET 10 gradually decreases to thereby increase the pulse density of the on-pulses from the rising edge of the rectangular pulse until the first half of the time width t1 thereof elapses and then gradually increases to thereby decrease the pulse density thereof as it comes closer to the falling edge of the rectangular wave pulse during the second half of the time width t1 thereof.

When the +side PDM signal is supplied from the CPU 2 to the FET 9 while a rectangular wave pulse is output to the center tap of the primary winding 22 of the transformer 21, the FET 9 is turned on during an output period of each on-pulse, so that one terminal (i.e. dotted side) of the primary winding 22 is grounded, thus inducing a voltage in one terminal (dotted side) of the secondary winding 23. Likewise, when the-side PDM signal is supplied from the CPU 2 to the FET 10 while a rectangular wave pulse is output to the center tap of the primary winding 22 of the transformer 21, the FET 10 is turned on during the output period of the on-pulses, so that the other terminal (non-dotted side) of the secondary winding 23 is grounded, thus inducing a voltage in the other terminal (non-dotted side) of the secondary winding 23. Accordingly, as shown in FIG. 2, when the on-pulses are supplied to the gate of the FET 9 during the output period of the rectangular wave pulses, a positive stimulation signal is output in the form of pulses, while when the on-pulses are supplied to the gate of the FET 10 during the output period of a rectangular wave pulse, a negative stimulation signal is output in the form of pulses.

Thus, across the output electrodes 24 are repeatedly generated stimulation signals having a voltage level proportional to the amplitude A1, the stimulation signals being obtained by subjecting the rectangular wave pulses of the variable output signals to pulse density modulation through the FETs 9, 10. These stimulation signals exhibit a group S of pulses, generated at every period T, the group having the time width t1, the pulse group S alternately having a positive voltage and a negative voltage. The off-time interval t2 of the on-pulses gradually decreases to increase the pulse density of the on-pulses from the rising edge of the rectangular wave pulse group S until about the middle of the pulse group S and then gradually increases to decrease the pulse density thereof until the falling edge of the rectangular wave pulse group S. As long as the stimulation signals are being output, a built-in timer (not shown) inside the CPU 2 continues to count time, displaying the time on the segment LED 7.

FIG. 3 and FIG. 5 show waveforms of such stimulation signals generated. The stimulation signals shown here as sample signals are defined by rectangular wave pulse groups of recurring frequency 2.74 KHz (recurring period $T_0$=365 μsec). Each on-pulse which serves as a high frequency component, having a uniform time width of 2 μsec is contained within the stimulation signals at the varying time interval in the range of from 2 to 15 μsec due to PDM. FIG. 3 shows a comparative waveform in the case where a 500 Ω dummy resister is connected as a load across the output electrodes 24. FIG. 4 shows an enlarged view of the waveform of FIG. 3 where its abscissa axis (time) is enlarged. In FIGS. 3 and 4, substantially the same waveform as that of the stimulation signals shown in FIG. 2 is generated across the dummy resister. In contrast, FIG. 5 shows a voltage waveform across the output electrodes 24 in the case where the electrodes 24 are attached to a human waist and then energized. In that case, a human body functions as if it were a capacitive element, so that when the off-time interval t2 gradually narrows between the on-pulses as the positive high frequency components applied across the output electrodes 24, electrical charges charged into a capacitive human body gradually increases, thus causing an abrupt change in the voltage waveform applied to the output electrodes 24. As a result, the voltage waveform turns from the negative to the positive. Subsequently, when the off-time interval t2 gradually widens between the on-pulses as the positive high frequency components applied across the output electrodes 24, electrical charges charged into a capacitive human body gradually decreases, thus causing a gradual and moderate change in the voltage waveform applied to the output electrodes 24 at its positive peak. Thereafter, the off-time intervals t2 of the on-pulses as the negative high frequency components gradually widen and gradually narrow in the similar manner when these on-pulses are applied across the output electrodes 24, so that the change in electrical charges charged into a human body becomes gradually abrupt and then moderate, so that the voltage waveform of the output electrodes 24 turns from the positive to the negative to become gradually moderate in change at its negative peak. Thus, a low frequency of substantially sinusoidal waveform, as shown in FIG. 5, is produced due to the change in charging and discharging voltages to a human body with the on-pulses serving as positive and negative high frequency components being carried on the low frequency of such sinusoidal waveform.

In other words, when the off-time interval t2 between the on-pulses is large (i.e., on-pulse frequency is low), electrical charges or discharges relative to the equivalent electrostatic capacity of the human body are small in quantity to make change of voltage waveform moderate across the output electrodes 24. On the other hand, when the off-time interval t2 between the on-pulses is small (i.e., on-pulse frequency is high), electrical charges or discharges relative to the equivalent electrostatic capacity of the human body are large in quantity to make change of voltage waveform abrupt. As a result, the stimulation signals are modulated into the sinusoidal low frequency signals to be formed into waveforms in which high frequency rectangular wave signals are carried on these low frequency signals. The low frequency signals thus distorted into sinusoidal waveforms can provide extremely soft feeling of stimulation as compared with a rectangular wave having the same current and frequency. Furthermore, since on the stimulation signals are carried high frequency rectangular wave signal components obtained by switching operation of the FETs 9, 10, the therapeutic effects are enhanced by the components.

Moreover, the time width of each on-pulse is uniform and the pause period (off-time interval t2) between the on-pulses is varied by the stimulus generator means 8, whereby the apparatus produces no wider on-pulses such as those produced by PWM in the conventional apparatus. As a result, a charging current is supplied little by little to the equivalent electrostatic capacity of a human body, so that a charging quantity (energizing quantity) rises gradually. Consequently, cenesthesia of softer stimulation can be obtained even by high frequency on-pulse components.

In order that a waveform of the stimulation signals may exhibit low frequency components of an approximately sinusoidal waveform as illustrated in FIG. 5, when applied to a human body, it is desirable that the rectangular wave pulse groups S each comprising a plurality of on-pulses and defining the uniform time width t1 are alternately positive and negative; and the density of the on-pulses gradually increases approximately corresponding to the amplitude increments of a sine function $\sin\Omega t$ in the range of $0<\Omega t<\pi/2$ (i.e., the off-time interval t2 between the on-pulses gradually narrows approximately inversely with the above amplitude increments from the rising edge of the rectangular wave pulse group S until about the middle thereof), and then, the density of the on-pulses gradually decreases, following the inverse order of the above density increments (i.e., the off-time interval t2 widens approximately inversely with the above pulse density). It is desirable that the stimulus generator means 8 is configured so as to operate as the above-mentioned manner. It should be noted, however, that the off-time interval t2 between the on-pulses can be varied at random by a time interval varying means or a control sequence of the CPU 2. In addition, not only sinusoidal waves but various waves such as triangular waves or pre-distorted waves can also be envisaged, thus enabling a unique stimulation feeling different from the one provided by sinusoidal waves.

When the above-mentioned stimulation signals are repeatedly applied to a human body, the latter may get accustomed to these signals, resulting in a drawback of lowering the therapeutic effects such as the removal or alleviation of pains. In a further embodiment of the invention, the control sequence of the CPU 2 may comprise pauses so that the stimulation signals are temporarily stopped during the output of a stimulation pause period setting signal. Another way to prevent inurement to stimulation is to vary the amplitude of the stimulation signal. In response to the strong stimulation command signal output from the CPU 2 to the output variable circuit 11, as shown at a right side in FIG. 2, a rectangular pulse of larger amplitude A2 than the predetermined amplitude A1 is temporarily supplied by the output-variable circuit 11 to the stimulus generator means 8. Thus, stronger stimulation signals i.e. pulse groups S' of greater amplitudes are temporarily applied to the human body, so that the above-mentioned drawback is eliminated.

Figure 2:
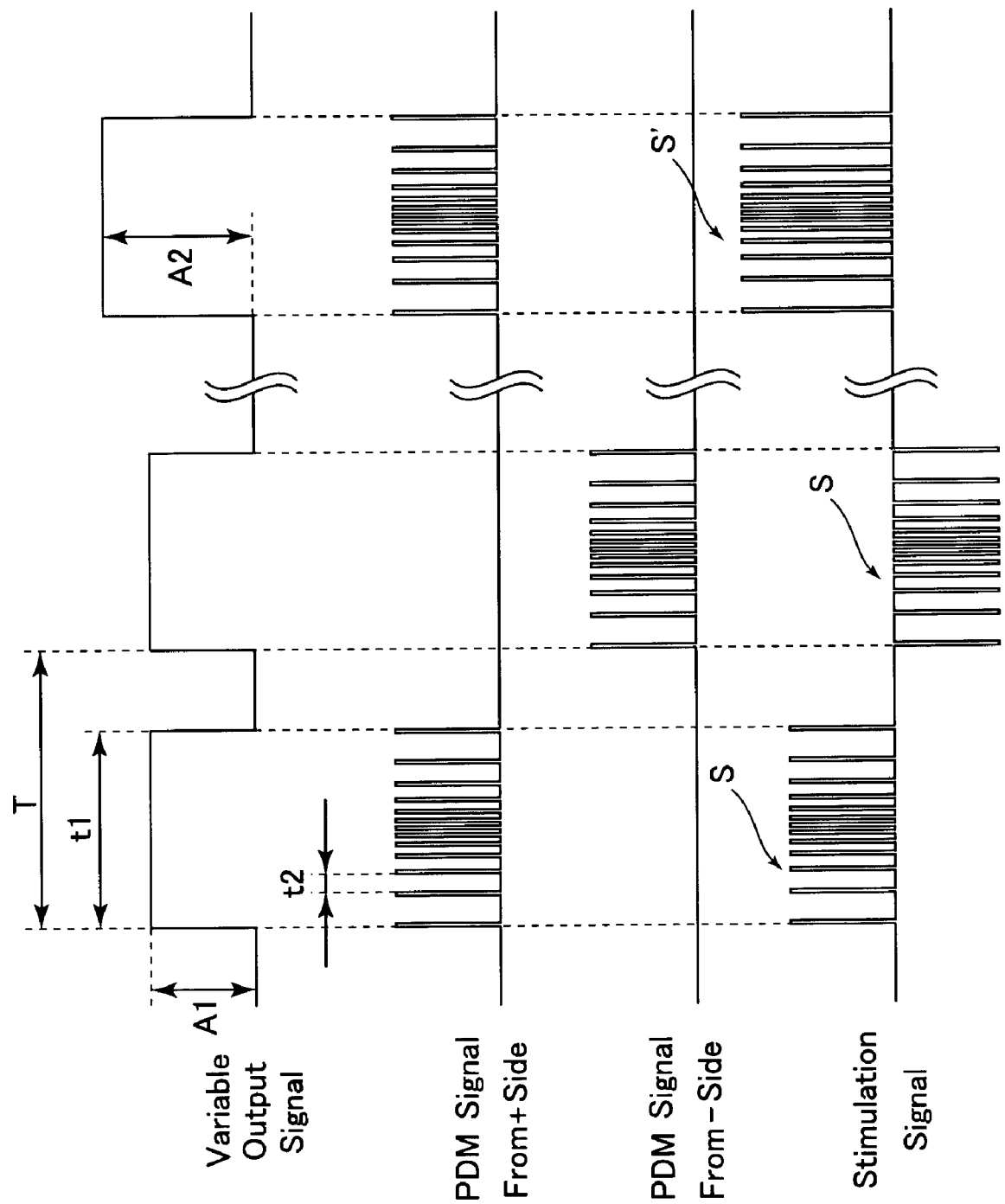
FIG. 2 is a waveform diagram showing waveforms at several points in the apparatus of FIG. 1.
Figure 6:
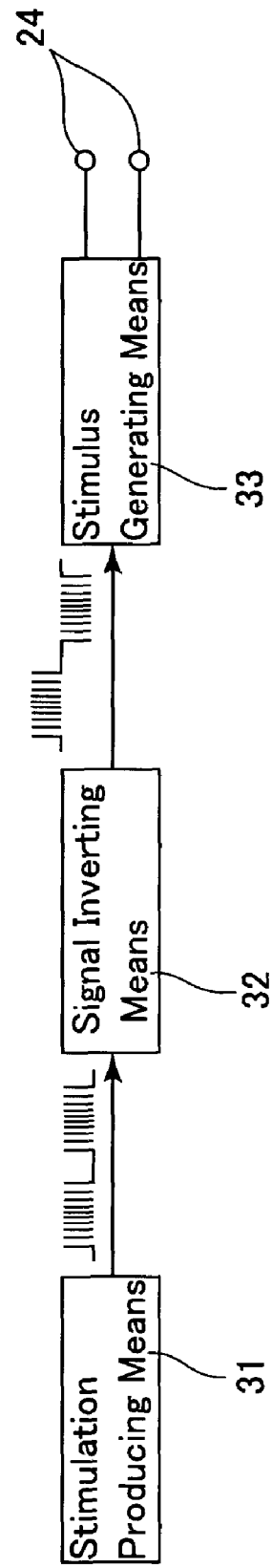
FIG. 6 is a block diagram showing a modified embodiment.
Figure 7:
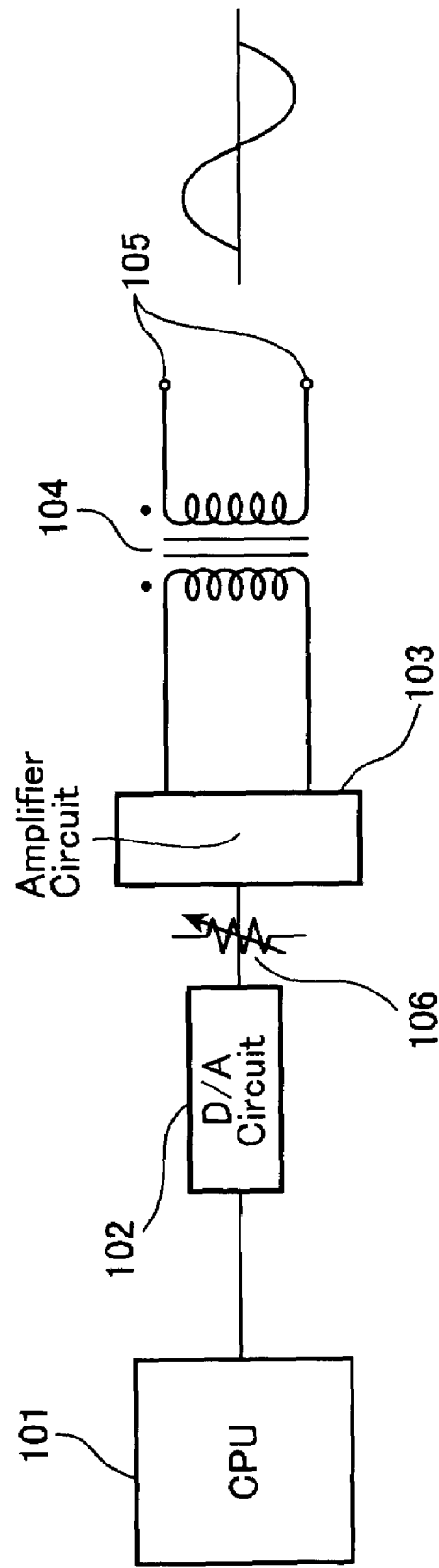
FIG. 7 is a circuit diagram of a substantial part showing a conventional apparatus.

In the meantime, a means for obtaining the rectangular wave pulse groups that are subjected to pulse density modulation as shown in FIG. 2 is not limited to the one shown in FIG. 1. As shown in FIG. 6, for example, the above means may comprise a stimulus producing means 31, a signal inverting means 32 and a stimulus generator means 33. The stimulus producing means 31 outputs rectangular wave pulse groups at preset time intervals, each of said pulse groups having a uniform time width, comprising a plurality of on-pulses of varying pulse densities. The signal inverting means 32 inverts the rectangular wave pulse groups alternately to positive and negative every time each rectangular wave pulse group with a uniform time width is output from the stimulus producing means 31. The stimulus generator means 33 amplifies and outputs the output signals from the signal inverting means 32 as stimulation signals. Thus, without the need of producing the rectangular wave pulses with a uniform time width t1, the rectangular wave pulse groups S are allowed to appear alternately in the positive and in the negative like the formation shown in FIG. 2. Besides, the off-time interval t2 between the respective on-pulses gradually narrows to raise the pulse density of the on-pulses from the rising edge of the rectangular wave pulse group S until about the middle of the time width t1 of the rectangular wave pulse group S and then gradually widens to lower the pulse density thereof until the falling edge of the rectangular wave pulse, so that thus generated stimulation signals can be applied to a living body. As described above, the stimulation pause period and amplitude of the rectangular wave pulse group S may be arbitrarily varied by the stimulus producing means 31. Alternatively, the signal inverting means 32 may be omitted if the stimulus producing means 31 can generate alternately positive and negative rectangular wave pulse groups S.

As is apparent from the foregoing, the first embodiment of the invention proposes a living body stimulating apparatus for applying an electric stimulus to a living body by attaching the conductor element 24 to the living body to allow an electric current to flow from the conductor element 24 to the living body, wherein the apparatus comprises the stimulus generator means 8 for outputting repeatedly the rectangular wave pulse groups S as stimulation signals to the output electrodes 24, said stimulus generator means 8 outputting the stimulation signals obtained by varying the density of a plurality of the on-pulses constituting the rectangular wave pulse groups S during the output period t1 of the rectangular wave pulse groups S.

Moreover, when the rectangular wave pulse groups S containing a plurality of the on-pulses are repeatedly output across the output electrodes 24 as stimulation signals, the human body functions to have a capacitive impedance and thus the impedance is lowered when the on-pulses having higher frequency signal components are applied. The waveforms of the rectangular wave pulse groups S are distorted as a whole inside the human body, thus producing distorted waveforms of low frequency. Consequently, softer feeling of stimulation can be given to the human body as compared with the rectangular wave pulse of the same current and frequency. In addition, as each rectangular wave pulse group S includes a plurality of signal components (on-pulses) of higher frequency than the recurrence frequency of the rectangular wave pulse, extensive therapeutic effects can be obtained by the signal components.

Furthermore, as the stimulus generator means 8 arbitrarily varies the density of a plurality of the on-pulses constituting the rectangular wave pulse groups S, the waveform of low frequency applied to the inside of the living body can be distorted into a desirable shape, corresponding to varied density of the on-pulses. Besides, since the time width of each on-pulse is constant and a pause period of the on-pulse (off-time interval t2) is varied by the stimulus generator means 8 during the output period of each rectangular wave pulse group S, there exist no on-pulses wider than other on-pulses, so that a charging current is supplied little by little to the equivalent electrostatic capacity of the human body to raise a charged quantity therein slowly and thus the cenesthesia of softer stimulation can be obtained.

Specifically in the stimulus generator means 8 of the present embodiment, the rectangular wave pulses defining pulse groups S each having a predetermined time width t1 as a whole are allowed to appear alternately in the positive and in the negative, and the density of the on-pulses gradually increases during the first half of the said time width t1 and then gradually decreases during the second half thereof. Thus, the stimulation signals obtained by varying the density of a plurality of the on-pulses are output by the stimulus generator means 8.

When the stimulus generator means 8 outputs such stimulation signals, each of the rectangular wave pulse groups S has its waveform distorted, so that the stimulation signals are allowed to take waveforms where high frequency on-pulses are superimposed on the signals which are approximate to low frequency sinusoidal waves. Consequently, extreme soft feeling of stimulation can be obtained as compared with the rectangular wave pulse of the same current and frequency.

Moreover, in the present embodiment, the stimulus generator means 8 outputs stimulation signals in which the time width t1 of the rectangular wave pulse group S is at least 100 times larger than that of the individual on-pulse. As s result, as each on-pulse applied to a human body is output with the time width shorter than one hundredth of the rectangular pulse group S comprising a group of the on-pulses, high frequency signal components are extremely effectively applied to a human body during the generation of the low frequency signal components.

More specifically, the stimulus generator means 8 of the present embodiment, as specifically shown in FIG. 1, comprises: the FETs 9, 10 serving as switching means for on-off switching of the rectangular wave pulse to thereby produce the rectangular wave pulse group S which includes a plurality of signal components having higher frequency than the rectangular wave pulse; and the CPU 2 serving as a pulse density control means for supplying the gates of the FETs 9, 10 with PDM digital signals (or +side PDM signals and-side PDM signals) for switching the FETs 9, 10.

Accordingly, in order to distort each rectangular pulse group S of the stimulation signals, you have only to supply the FETs 9, 10 serving as switch means with such on-off PDM digital signals, and thus there is no longer any need for conventional circuits (such as the conventional D/A circuit 102 and the amplifier circuit 103) for obtaining sinusoidal waveforms. As a result, whilst the conventional circuits for outputting sinusoidal waves would require dozens of components such as transistors, resisters and capacitors, the apparatus according to the present embodiment of the invention only requires a pair of FETs 9, 10, thus extremely simplifying the configuration of the stimulus generator means 8 serving as the stimulation signal output circuit. Further, the pulse density modulation using the switch means exhibits extremely high power efficiency, as is well demonstrated by the current control of brush-less DC servomotors.

It should be further noted that the CPU 2 of the present embodiment comprises strong stimulation command means for allowing the stimulus generator means 8 to temporarily output the rectangular wave pulse of greater amplitude A2 than the preset amplitude A1 when the strong stimulation mode is active. The strong stimulation command means enables the applying of strong stimulation signals i.e. rectangular wave pulse groups S' of larger amplitude. This can prevent a human body from getting accustomed to the stimulation signals. Alternatively, the apparatus may be modified to generate a rectangular wave pulse whose amplitude is randomly variable. Likewise, the pause period of the stimulation signal can also be randomly varied. In either case, a human body is more effectively prevented from getting accustomed to the stimulation signals. As the control sequence running on the CPU carries out the respective functions of the above strong signal command means, stimulation pause command means as well as the pulse density modulation means, the circuitry is able to have a less complicated configuration than those known in the prior art.

The present invention is not limited to the above embodiments and various modifications are possible. The recurrence frequency of the rectangular pulse wave group S, the time width t1 of each rectangular wave on-pulse group, the pulse density i.e., the off-time interval t2 between the on-pulses may be chosen relatively freely according to the various needs.

What is claimed is:

1. A living body stimulating apparatus for applying an electric stimulus to a living body, said apparatus comprising conductor elements to apply a stimulation signal to said living body by allowing an electric current to flow from the conductor elements to said living body, which comprises: a stimulus generator means for outputting rectangular wave pulse groups repeatedly to said conductive elements as stimulation signals, said stimulus generator means outputting stimulation signals formed by varying the density of a plurality of on-pulses constituting the rectangular wave pulse groups during an output period of said rectangular wave pulse groups, so that said rectangular wave pulse groups defining pulse groups are alternately positive and negative, while the density of said on-pulses gradually increases from a rising edge of the rectangular wave pulse group until about the middle of a predetermined time width thereof and then gradually decreases until a falling edge of the rectangular pulse group.

2. A living body stimulating apparatus according to claim 1, wherein said stimulus generator means outputs said stimulation signals so that a time width of said rectangular wave pulse group may be at least 100 times wider than that of said on-pulse.

3. A living body stimulating apparatus according to claim 1, wherein said stimulus generator means is provided with a switching means for generating a rectangular pulse group containing a plurality of higher frequency signal components than the rectangular wave pulse by on-off switching of the rectangular pulse and a pulse density controlling means for supplying PDM digital signals for switching the switching means to the switching means.

4. A living body stimulating apparatus according to claim 3, wherein said pulse density controlling means comprises a control sequence installed inside a CPU.

5. A living body stimulating apparatus according to claim 3, further comprising a strong stimulation command means for temporarily outputting said rectangular wave pulse of a larger amplitude than a predetermined one.

6. A living body stimulating apparatus according to claim 5, wherein said strong stimulation command means comprises a control sequence installed inside a CPU.

7. A living body stimulating apparatus according to claim 1, further comprising a stimulation pause command means for temporarily stopping the output of said stimulation signals.

8. A living body stimulating apparatus according to claim 7, wherein said stimulation pause command means can vary a stimulation pause period at random.

9. A living body stimulating apparatus according to claim 7, wherein said stimulation pause command means comprises a control sequence installed inside a CPU.

10. A living body stimulating apparatus according to claim 1, wherein an amplitude of said rectangular wave pulse can be varied at random.

11. A living body stimulating apparatus according to claim 1, wherein said stimulus generator means outputs the stimulation signals in such a manner that during a time width that is periodically generated, positive rectangular wave pulse groups comprising a plurality of the on-pulses and negative rectangular wave pulse groups comprising a plurality of the on-pulses are alternately generated, and the time width of each on-pulse is kept constant, while a pause period between the on-pulses is varied in each of the positive and negative rectangular wave pulse groups, so that the density of said on-pulses gradually increases approximately corresponding to the amplitude increments of a sine function sine in the range of $0<\Omega t<\pi/2$ from a rising edge of the rectangular pulse group until, about the middle of a predetermined time width thereof and then gradually decreases following the inverse order of the above density increments until a falling edge of the rectangular pulse group.

* * * * *